United States Patent [19]
Bell et al.

[11] Patent Number: 5,273,543
[45] Date of Patent: Dec. 28, 1993

[54] SAFETY NEEDLE SYRINGE

[75] Inventors: Jon S. Bell, Midland Park; Richard Eisenring, Ringwood; Niall Sweeney, Rutherford, all of N.J.

[73] Assignee: Becton, Dickinson and Company, Franklin Lakes, N.J.

[21] Appl. No.: 990,234

[22] Filed: Dec. 14, 1992

[51] Int. Cl.⁵ .............................................. A61M 5/00
[52] U.S. Cl. .................................... 604/110; 604/195
[58] Field of Search ............... 604/110, 187, 195, 198, 604/263

[56] References Cited
U.S. PATENT DOCUMENTS

| | | |
|---|---|---|
| 3,828,775 | 8/1974 | Armel . |
| 4,026,287 | 5/1977 | Haller . |
| 4,650,468 | 3/1987 | Jennings, Jr. ................ 604/110 |
| 4,675,005 | 6/1987 | DeLuccia ..................... 604/110 |
| 4,838,870 | 6/1989 | Haber et al. ................. 604/187 |
| 4,908,022 | 3/1990 | Haber ......................... 604/195 |
| 4,935,015 | 6/1990 | Hall ............................ 604/195 |
| 4,950,241 | 8/1990 | Ranford ................... 604/195 X |
| 4,950,251 | 8/1990 | Haining ....................... 604/195 |
| 4,995,874 | 2/1991 | Strickland .................... 604/195 |
| 5,007,903 | 4/1991 | Ellard .......................... 604/195 |
| 5,098,402 | 3/1992 | Davis .......................... 604/195 |
| 5,112,315 | 5/1992 | Gloyer et al. ................ 604/195 |
| 5,152,750 | 10/1992 | Haining ................... 604/110 X |

Primary Examiner—John D. Yasko
Attorney, Agent, or Firm—John L. Voellmicke

[57] ABSTRACT

A safety needle syringe includes a barrel having an inside surface defining a chamber, an open proximal end and a distal end. A movable needle carrier is positioned in fluid-tight engagement with the inside surface of the barrel and includes a distal end, a proximal end and a passageway there through in fluid communication with the chamber. A needle cannula projects outwardly from the distal end of the carrier and includes a lumen in fluid communication with the passageway. A plunger assembly is slidably positioned in fluid tight engagement with the inside surface of the barrel. Structure is providing for allowing the distal end of the plunger to engage the carrier for allowing axially directed and rotational forces applied to the proximal end of the plunger to be transmitted to the carrier. Control structure is provided for helping to prevent movement of the carrier with respect to the barrel during normal use of the syringe while the control structure is in a first locked position and for allowing the carrier to be moved proximally into the chamber through forces applied to the plunger while the control means is in a second unlocked position.

15 Claims, 8 Drawing Sheets

SAFETY NEEDLE SYRINGE

BACKGROUND OF THE INVENTION

1. Field of the Invention

The present invention relates to hypodermic syringes having structure to help prevent accidental needle sticks. More particularly, the present invention relates to a safety needle syringe capable of withdrawing the hypodermic needle into the syringe barrel after use.

2. Description of Related Information

Generally speaking, a syringe includes a cylindrical barrel, commonly made of thermoplastic material or glass, having a distal end connected to a sharpened needle cannula and a proximal end adapted to receive a stopper and plunger assembly.

In recent years there has developed an increased concern regarding the transfer of disease, infection or the like to syringe users and health care professionals who accidentally, or through negligent handling, stick themselves with hypodermic needles while disposing of used hypodermic syringe products. In many areas in a hospital, where needle cannula products are used, disposal bins are provided so that a syringe or other needle cannula product may be immediately discarded in a safe rigid container. However, there are areas of medical practice such as emergency rooms, or other areas where disposal containers are not readily available or practical, where products having self-contained safety features are desirable. In theory, after such a syringe is used to inject medication or for another purpose, a safety device contained within the syringe is activated to prevent further contact with the sharp needle tip. One type of safety syringe includes structure which allows the withdrawal of the hypodermic needle into the syringe barrel to minimize the chance of further contact with the sharp needle tip. The syringe, in this condition, can be more safely transported to a disposal system.

Such a syringe is taught in U.S. Pat. No. 4,026,287. This patent teaches a syringe having a frangible zone which allows separation of the forward wall of the barrel, which is connected to the hypodermic needle, from the side wall of the barrel. The syringe also contains structure on the interior of the forward wall and the exterior of the piston for selectively attaching the piston to the forward wall so that the user can forcibly twist the piston to break the frangible means and draw the forward wall, including the hypodermic needle, into the syringe barrel. This design requires a compromise in the design of the syringe barrel. The barrel must be strong enough to remain intact during normal use yet weak enough to be sheared apart by any user regard less of strength.

U.S. Pat. No. 3,828,775 teaches a retracting needle syringe wherein the needle assembly is contained within the syringe barrel before use and is withdrawn back into the barrel after use. Designs of this type have a disadvantage in that the user cannot change needle size and the decision regarding what size needle will be used with the syringe must be made at the time the syringe is purchased.

In many situations, the decision regarding which needle to use is made at the time of injection. More viscous medications may require a large needle. Less viscous medications may be delivered with a smaller needle which is believed to be less painful. Also, the depth of injection may be different depending on the therapy and the portion of the body being injected.

U.S. Pat. No. 4,675,005 teaches a retracting needle syringe wherein the needle is held at the distal end of the barrel through interaction of mating threads on the exterior of the needle hub and the interior of the distal barrel opening. This syringe relies on a torque or rotational force supplied by the user to secure the needle in an extended position and reversal of this procedure to withdraw the needle back into the barrel. Like many designs, including those wherein the needle is retained by a frictional interference fit, this design requires substantially the same force to install as to remove. Accordingly, the needle must be secure enough to withstand normal use which may include puncturing rubber vial stoppers, and still be easy enough to unsecure by any user. Without a lock or additional structure the holding force is, in these many designs, substantially equal to the removal or withdrawal force. Also, in designs which rely on rotational force applied through the plunger-rod to tightly secure the needle in the extended position, the user must be careful not to aggressively turn the plunger rod in the wrong direction when attempting to loosen the needle. In this case the needle will be more tightly secured and thus more difficult to remove.

Although the prior art teaches many useful and different syringe assemblies having the capacity to withdraw the needle into the syringe barrel after use, there still exists a need for a simple, straight-forward, reliable, easily fabricated safety needle syringe which allows the user to change needles at the time of use and provides structure to withdraw the needle into the syringe barrel using substantially axial forces such as those used for drawing liquid into a syringe. There also exists the need for a safety needle syringe having locking structure for holding a needle in a position with respect to the barrel, which can be deactivated to lower the force required for withdrawal of the needle into the barrel.

SUMMARY OF THE INVENTION

A safety needle syringe of the present invention includes a barrel having an inside surface defining a chamber, an open proximal end and a distal end. A movable needle carrier is positioned in fluid tight engagement with the inside surface of the barrel at the distal end of the barrel. The carrier includes a distal end, a proximal end and a passageway there through in fluid communication with the chamber. A needle cannula projects outwardly from the distal end of the carrier. The needle cannula includes a distal end, a proximal end and a lumen therethrough in fluid communication with the passageway. A plunger is slidably positioned in fluid tight engagement with the inside surface of the barrel. The plunger includes a distal end and a proximal end extending outwardly from the open end of the barrel. Engagement structure is provided for allowing the distal end of the plunger to engage the carrier for allowing axially directed forces and rotational forces applied to the proximal end of the plunger to be transmitted to the carrier. Control structure is provided for helping to prevent movement of the carrier with respect to the barrel during normal use of the syringe while the control structure is in a first locked position. The control structure allows the carrier to be moved proximally into the chamber through forces applied to the plunger while the control structure is in a second unlocked position. Transition between the first locked position and the second unlocked position and withdrawing the cannula into the barrel is accomplished by at least two motions of the plunger with respect to the barrel, while the distal end of the plunger engages the carrier. The first motion being a rotational motion to rotate the carrier with respect to the barrel through an acute angular rotation followed by a second proximally directed motion to move the carrier into the barrel far enough so that the distal end of the cannula does not extend beyond the distal end of the barrel.

DETAILED DESCRIPTION

While this invention is satisfied by embodiments in many different forms, there are shown in the drawings and will be herein described in detail preferred embodiments of the invention with the understanding that the present disclosure is to be considered exemplary of the principles of the invention and is not intended to limit the scope of the invention to the embodiments illustrated. The scope of the invention will be measured by the appended claims and their equivalents.

Adverting to FIGS. 1-10, a safety needle syringe assembly such as syringe assembly 20 includes an elongate barrel 21 having an inside surface 22 defining a chamber 23. Barrel 21 also includes an open proximal end 25 and a distal end 27.

For the purposes of the description of the present invention, the term "distal end" is intended to refer to the end of the syringe from which the needle cannula projects, whereas the term "proximal end" is intended to refer to the end of the syringe closest to the holder of the syringe and furthest from the tip of the needle.

A movable needle carrier 28 is positioned in fluid-tight engagement with inside surface 22 of barrel 21 at distal end 27. The needle carrier includes a distal end 29, a proximal end 31 and a passageway 32 therethrough in fluid communication with chamber 23. The carrier includes circumferential groove 33 at its proximal end. Annular elastomeric ring 34 is positioned in groove 33 and contacts the inside surface of the barrel to help provide a fluid tight engagement between the inside surface of the barrel and the carrier.

A needle cannula 37 projects outwardly from distal end 29 of the carrier. Cannula 37 includes a distal end 38, a proximal end 39 and a lumen therethrough in fluid communication with passageway 32. The needle cannula in this embodiment includes sharpened distal tip 46 to facilitate use of the needle to pierce the skin for delivery of therapeutic liquids. In this embodiment the needle is removably attached to the carrier. Also in this embodiment, the needle cannula is part of a needle assembly 35 which includes needle cannula 37 and a hub 41. The needle hub and the carrier contain cooperating structure so that the needle assembly is removably attached to the carrier. The needle hub includes a frusto-conically shaped interior structure adapted to frictionally engage a tapered luer tip 43 at the distal end of the carrier. To further facilitate the engagement of the needle hub to the carrier, projections 44 on the proximal end of the hub engage an internal helical groove 45 of the carrier so that clockwise rotation of the needle with respect to the carrier causes projections to be drawn proximally along the helical groove to tighten and secure the frictional engagement of tapered luer tip 43 with the frusto-conically shaped recess of hub 41. The needle assembly described herein is a known and commercially available needle assembly, designed to cooperate with syringes or other fittings having male locking luer type fittings.

The present invention includes plunger means slidably positioned in fluid tight engagement with the inside surface of the barrel. In this embodiment plunger means includes an elongate plunger rod 47 and an annular sealing ring 49. The plunger rod is accessible outside of the proximal end of the barrel and is provided to move the sealing ring along the barrel to force fluid into and out of the chamber through the passageway. Disc shaped plunger rod flange 50 is provided as a convenient structure for applying force to move the plunger rod with respect to the barrel. Barrel flanges 51 are also provided to assist the user in providing axial force between the plunger rod and the barrel.

Figure 8:
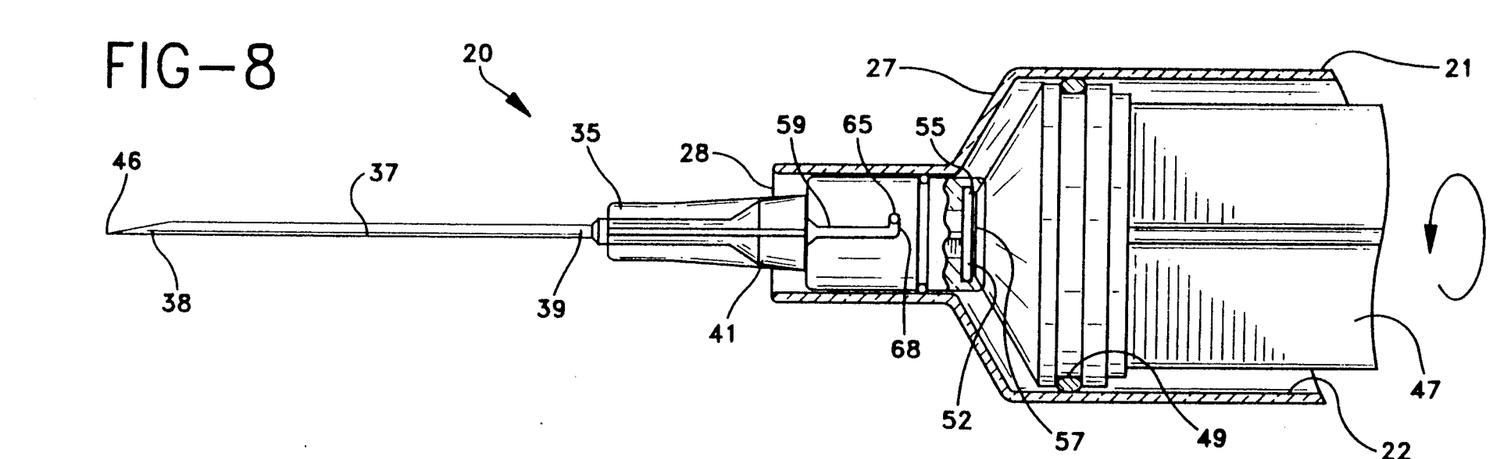
FIG. 8 is an enlarged partial cross sectional side elevation view of the syringe of FIG. 1 showing the plunger rod engaging the carrier.
Figure 9:
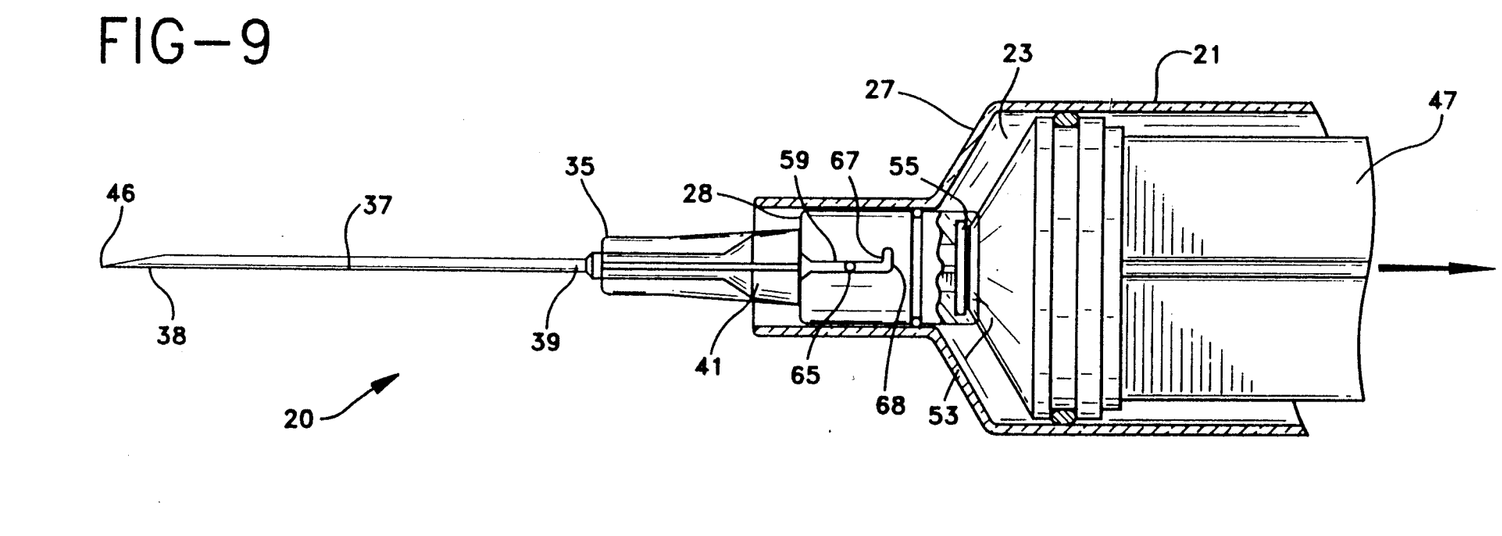
FIG. 9 is an enlarged partial cross-sectional side elevation view of the syringe of FIG. 1 showing the carrier partially withdrawn from the distal end of the barrel.
Figure 10:
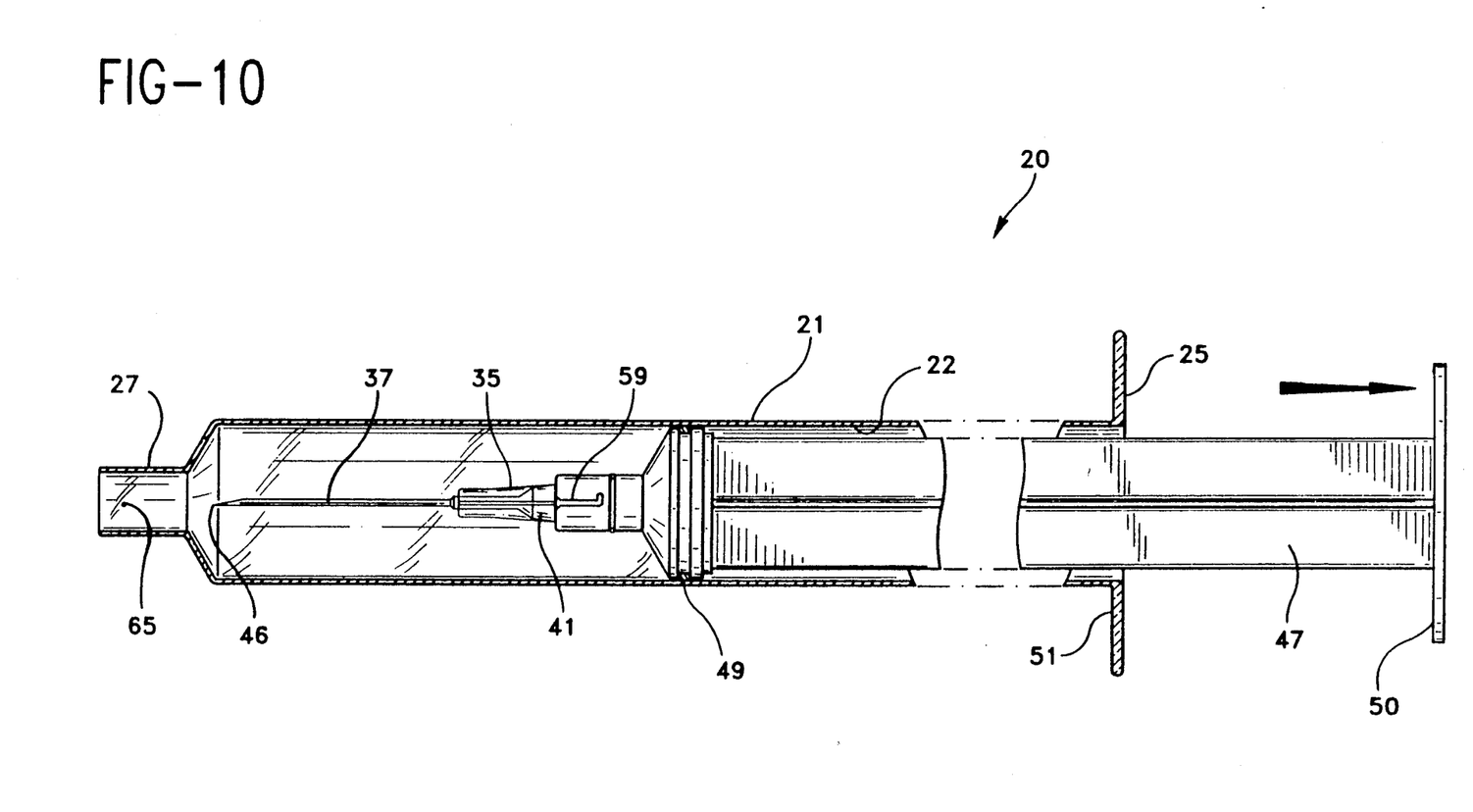
FIG. 10 is a partial cross sectional side elevation view of the syringe of FIG. 1 showing the carrier and needle withdrawn into the barrel.

Engagement means is provided for allowing the distal end of the plunger rod to engage the carrier for allowing proximally directed forces and rotational forces applied to the plunger to be transmitted to the carrier. In this embodiment, engagement means includes an enlarged projection 52 on the distal end of the plunger rod and a recess 53 in the proximal end of the carrier. Recess 53 includes inwardly projecting annular ring 55. Enlarged projection 52 includes undercut 57. The projection of the plunger rod and the recess of the carrier are designed to engage each other in a snap fit arrangement when axial force is applied to the plunger rod to force the distal end of the plunger rod, including the enlarged projection, against the carrier. When the plunger rod fully engages the carrier, as illustrated in FIGS. 8, 9 and 08, the inwardly projecting annular ring 55 of the recess will be positioned adjacent to undercut 57 of enlarged projection 52 so that the plunger rod can now transmit axial force to the carrier in a proximal direction.

Figure 1:
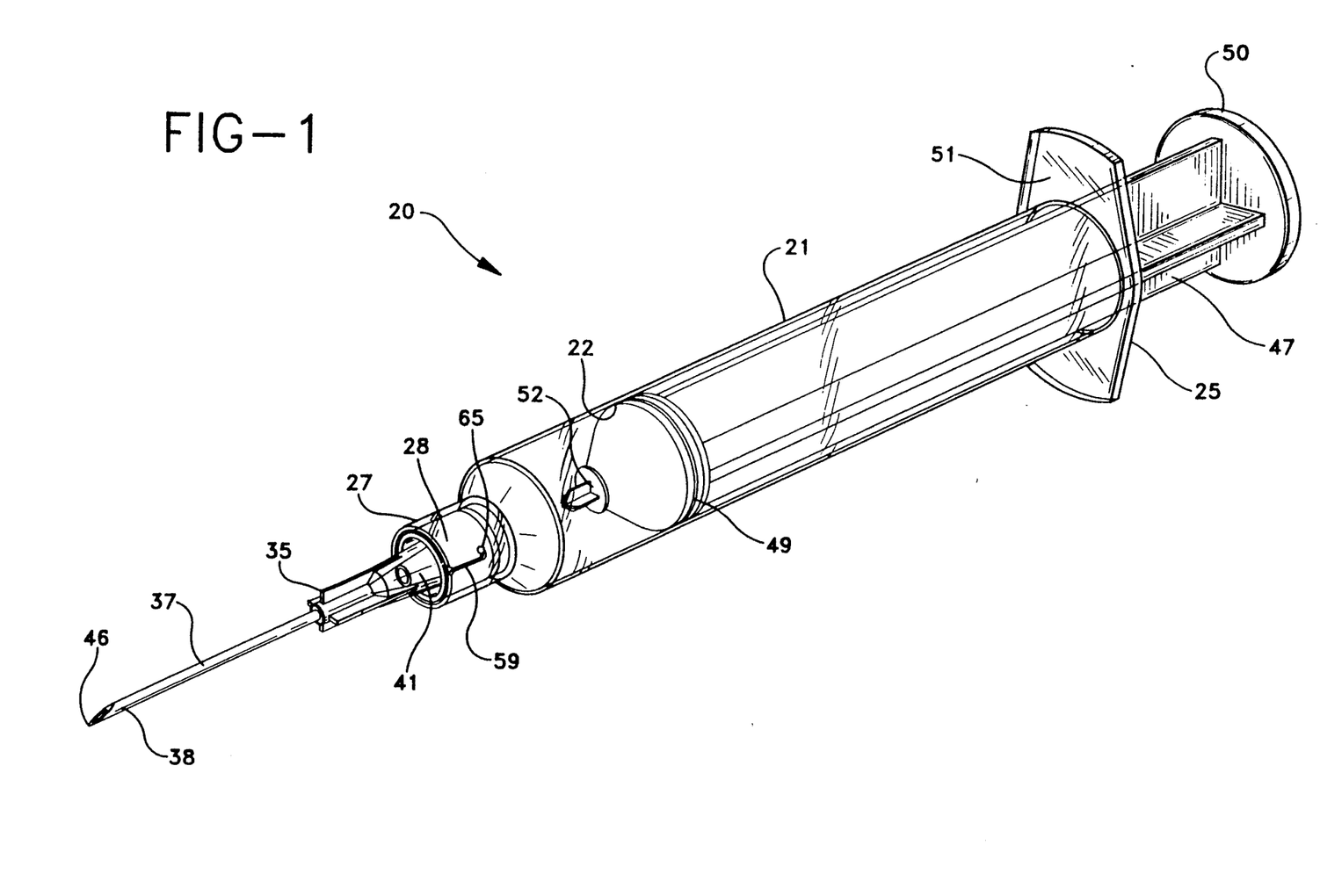
FIG. 1 is a perspective view of a preferred embodiment of the safety needle syringe of the present invention.
Figure 2:
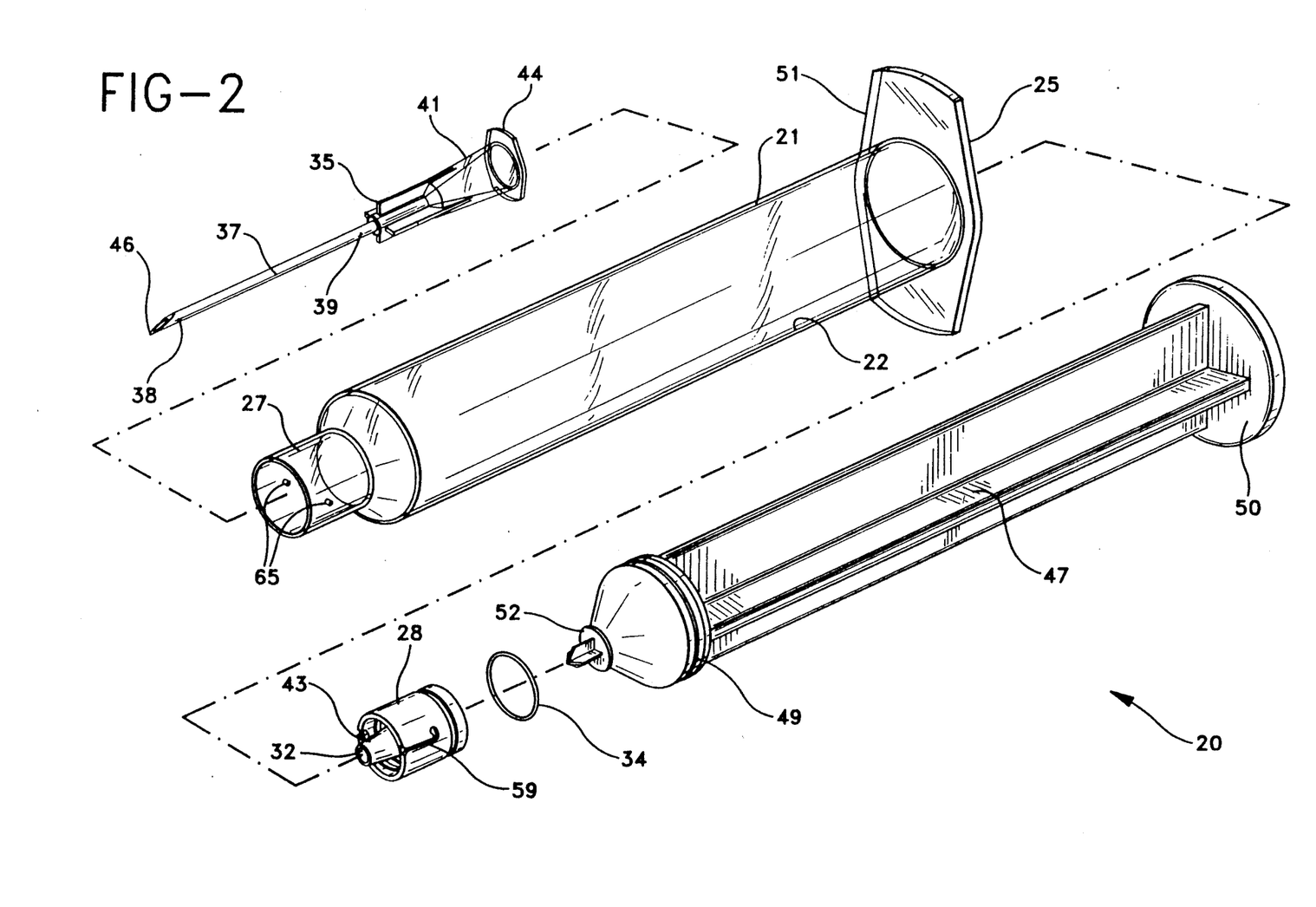
FIG. 2 is an exploded view showing the assembly of the syringe of FIG. 1.
Figure 3:
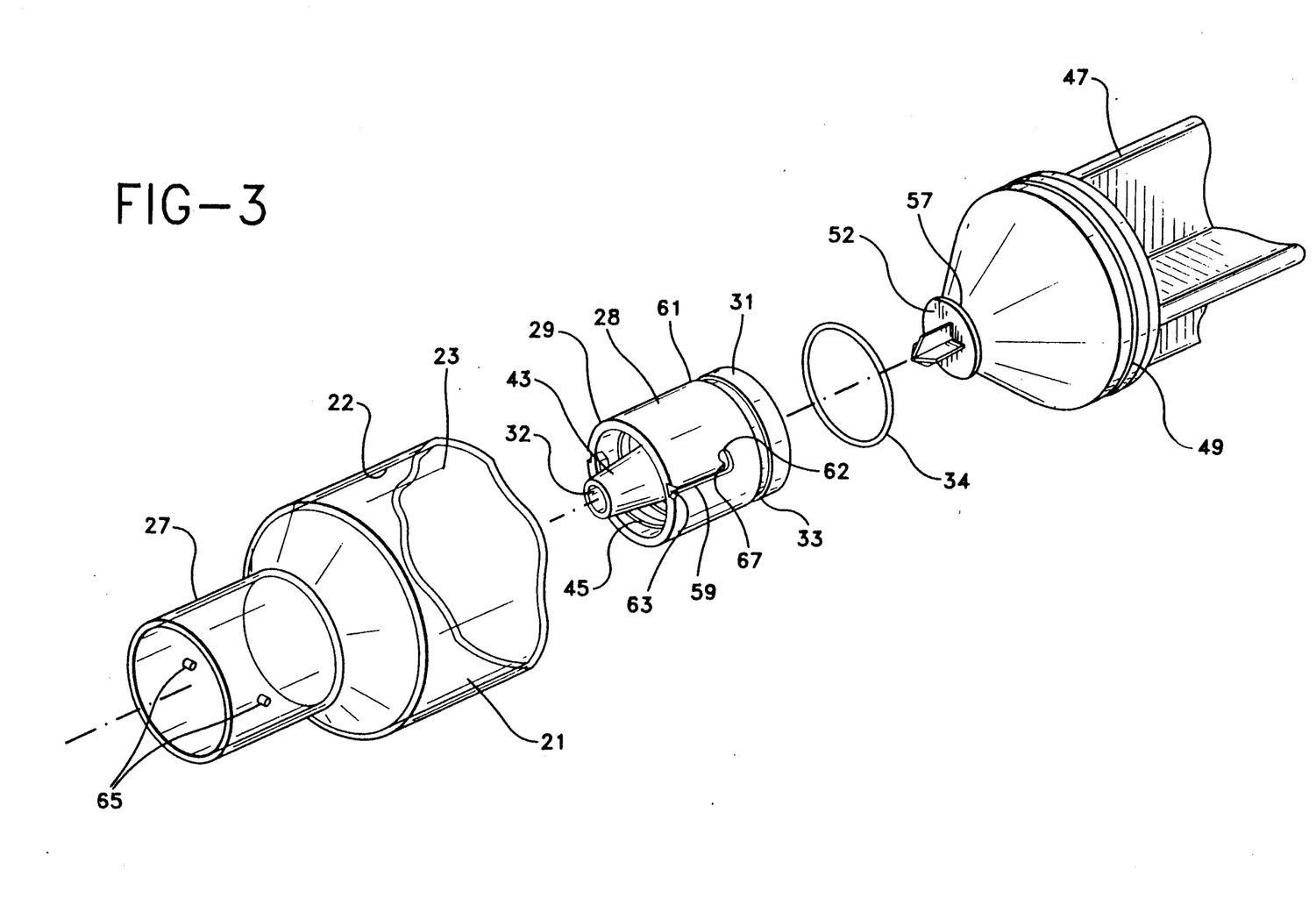
FIG. 3 is an enlarged partial view of FIG. 2 illustrating the distal end of the syringe barrel and the plunger rod, and the carrier.
Figure 4:
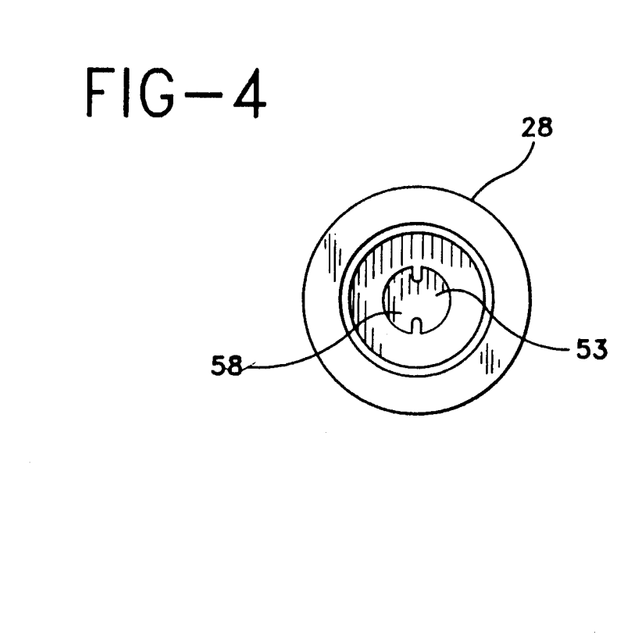
FIG. 4 is a side elevation view of the proximal end of carrier of FIG. 3.
Figure 5:
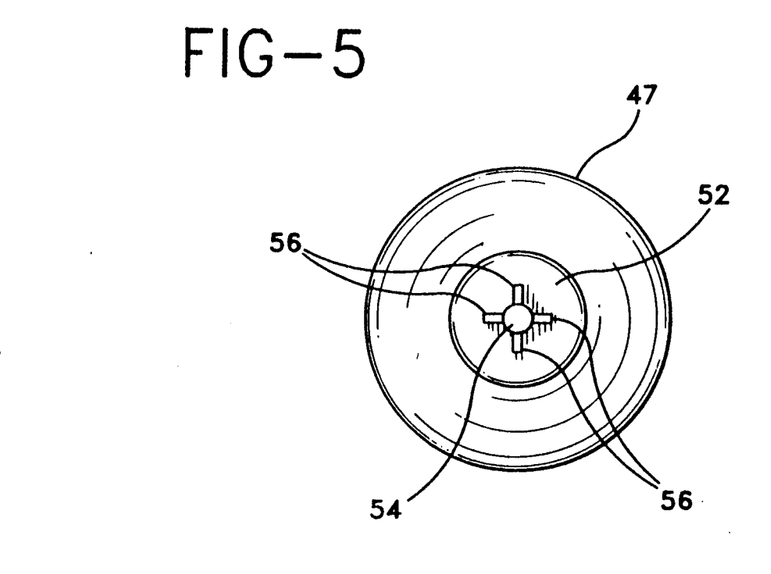
FIG. 5 is a side elevation view of the distal end of the plunger rod of FIG. 3.

Engagement means further includes distally extending boss 54 having one or more outwardly extending projections. In this embodiment there are four radially outwardly extending projections 56. Recess 53 also includes one more inwardly projecting protuberances. In this embodiment as best illustrated in FIG. 4, there are two radially inwardly projecting protuberances 58. Projections 56 on the boss and protuberances 58 in the recess of the carrier are adapted to engage each upon rotation of the plunger rod with respect to the carrier, when the plunger rod and the carrier are engaged, as described hereinabove.

An important feature of the present invention is that it allows the user to easily change needle assemblies at time of use to suit the type and viscosity of medication being delivered and the depth of injection required. Accordingly, one safety needle syringe of the present invention can work with many sizes of hypodermic needle assemblies to deliver medication or perform another fluid transfer function.

A deficiency of syringe designs which allow the user to change needle assemblies is that the components have to be held together securely enough to resist the relatively substantial forces involved with frictionally engaging a needle assembly hub to a syringe tip, and still be low enough to allow the user to force the needle assembly and connected structure into the barrel. Accordingly, if the carrier is frictionally engaged inside the syringe barrel it must be tight enough to resist axial and rotational forces involved with needle installation and removal yet not be so strong that the typical user cannot withdraw the carrier into the barrel. This same analogy applies to threaded carriers which must be able to resist the torque of needle installation and removal while being able to be easily withdrawn into the barrel. The present invention overcomes these shortcomings of prior art syringes by providing control means for helping to prevent movement of the carrier with respect to the barrel during normal use of the syringe while the control means is in a first locked position, and allowing the carrier to be moved proximally into the chamber through axial forces applied to the plunger rod while the control means is in a second unlocked position. Accordingly, another feature of the present invention is that the force used to remove and install a needle assembly will not substantially affect the force required to withdraw the needle assembly into the barrel.

Figures 6, 7:
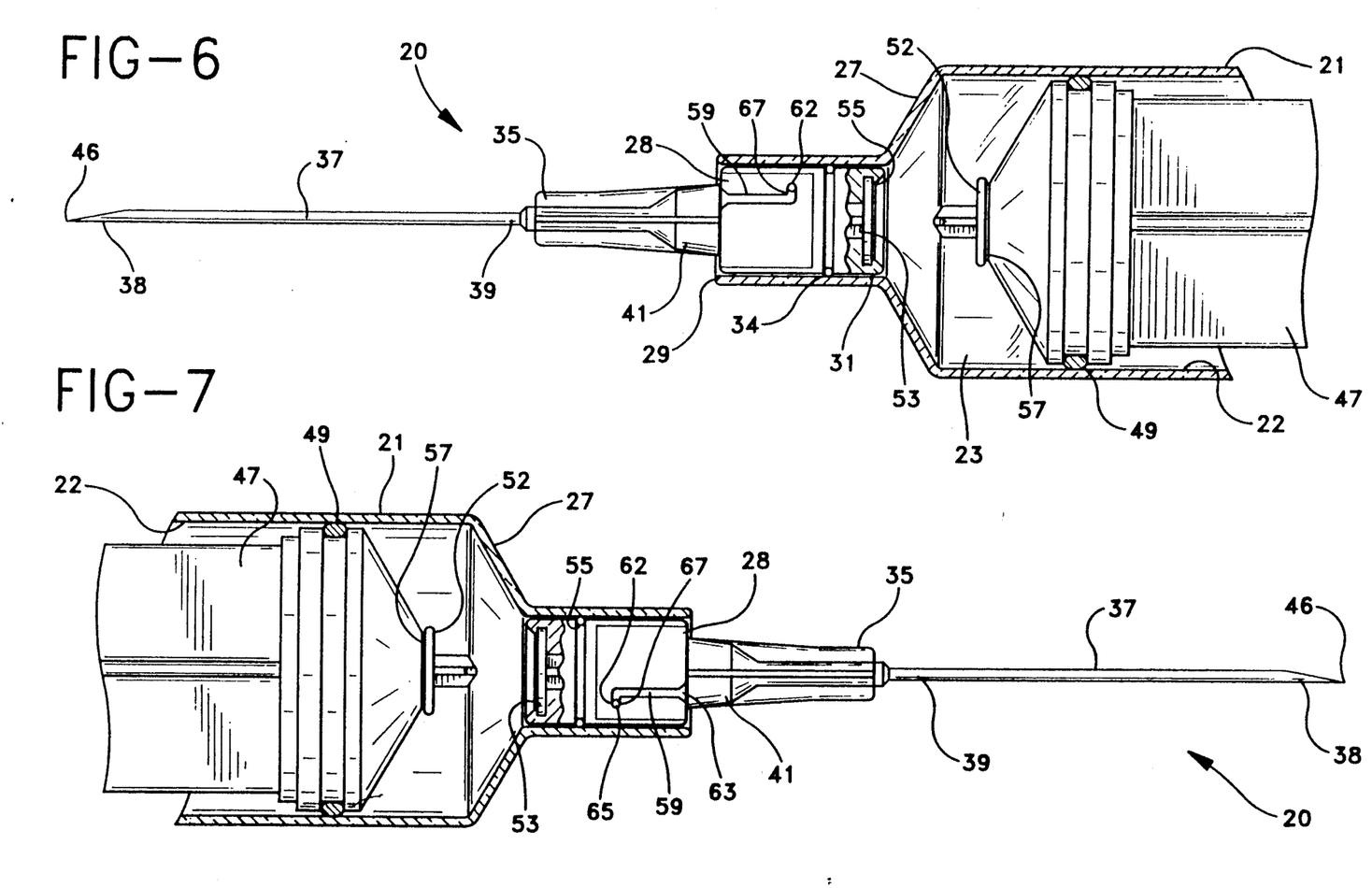
FIG. 6 is an enlarged partial cross sectional side elevation view of the syringe of FIG. 1.
FIG. 7 is an enlarged partial cross sectional side elevation view of the syringe of FIG. 1, as viewed from the back side or the opposite side as the view in FIG. 6.

In the present embodiment, control means includes grooves 59 on outside surface 61 of the carrier. Each groove includes a closed proximal end 62 and an open distal end 63. Inwardly directed projections 65 on the inside surface of the barrel are positioned within the grooves when the carrier is at the distal end of the barrel. In this embodiment, the projections are cylindrical having a circularly-shaped cross section. As illustrated in FIGS. 6 and 7, the projections prevent proximal and distal motion of the carrier with respect to the barrel when the projections are in closed ends 62 of grooves 59. Accordingly, substantial axial force can be applied in a proximal or distal direction, such as when installing or removing a needle assembly, without forcing the carrier into the barrel or removing it from the barrel and rendering the syringe unusable. Also, the relationship of the projections with the closed end of the grooves, as will be described in more detail hereinafter, resists rotational forces applied to the carrier when installing and removing a locking luer type needle. Although the present invention is illustrated with a locking luer type needle assembly and carrier, it is not restricted to this structure and can function with a luer slip type fitting provided on the carrier or an assembly where the needle is permanently attached to the carrier using epoxy or other suitable adhesive or other joining method. The locking luer type structure or luer slip type structure is preferred because it allows the user to change hypodermic needle assemblies.

In order to help resist rotational motion of the carrier away from closed end 62 of the grooves with respect to projections 65, each groove includes a restriction or area of reduced width 67 adjacent to closed end 62. The area of restriction or reduced width is smaller than the distance across projection 65 so that additional rotational force is required to move the carrier into and out of a position where projections 65 are positioned at closed ends 62 of the grooves. The restriction in this invention can also be an area of reduced depth in the groove adjacent to the closed end which is configured so that additional rotational force is required to move the carrier into and out of the position where projections 65 are positioned at closed ends 62 of the grooves.

The syringe of the present invention can be used in the same manner as a conventional hypodermic syringe following known and accepted safe usage procedures. At the end of the injection stroke which delivers medication to the patient, the user intentionally applies an additional axial force, preferably by squeezing flanges 51 and 50 toward each other, to force projection 52 on the plunger rod into engagement with recess 53 of the carrier, as illustrated in FIG. 8. A rotational force on the plunger rod will force the carrier to rotate through an acute angle as resisting force provided by the interference between the projections 65 and restriction 67 is overcome and the carrier will rotate until the projections are at base 68 of the groove and aligned with open end 63, as illustrated in FIG. 9. At this point the user may then pull the plunger in a proximal direction with respect to the barrel to withdraw the carrier and the needle assembly into the barrel as illustrated in FIG. 10. In this preferred embodiment the grooves are shaped such that only substantially axial motion of the plunger rod is required to engage the carrier to the plunger rod and to remove the carrier into the barrel of the syringe after the carrier has been unlocked from the barrel.

Further enhancements of the instant invention may include a plunger rod which is frangible so that that portion of the plunger rod projecting out of the syringe barrel can be physically disconnected from the remainder of the plunger rod so that the needle cannot be accidentally moved back through the distal end of the syringe to expose the sharp needle tip. Also, the portions of the plunger rod and carrier which interconnect can be designed so that the carrier misaligns itself with respect to the longitudinal axis of the syringe assembly when it is withdrawn into the syringe barrel. With the carrier misaligned, the needle cannot be forced out of the barrel after it is in the barrel because it is at an angle with respect to the longitudinal axis which causes it to embed itself into the forward wall of the syringe barrel when the plunger is advanced.

It is also within the purview of the present invention to include a threaded engagement between the plunger rod and the carrier. For example, the plunger may include a distal threaded projection which mates with a threaded recess in the carrier. The threads only function to connect the plunger rod and the carrier and the function of the syringe with respect to moving the needle assembly and carrier into the barrel is exactly as described above. With a threaded connection the threads should be in a direction to allow the user to rotate the carrier in the proper direction for unlocking. A wide variety of structures are capable of allowing the engagement of the plunger rod with the carrier and those structures described hereinabove are representative of these many possibilities which are within the purview of the present invention.

Figure 11:
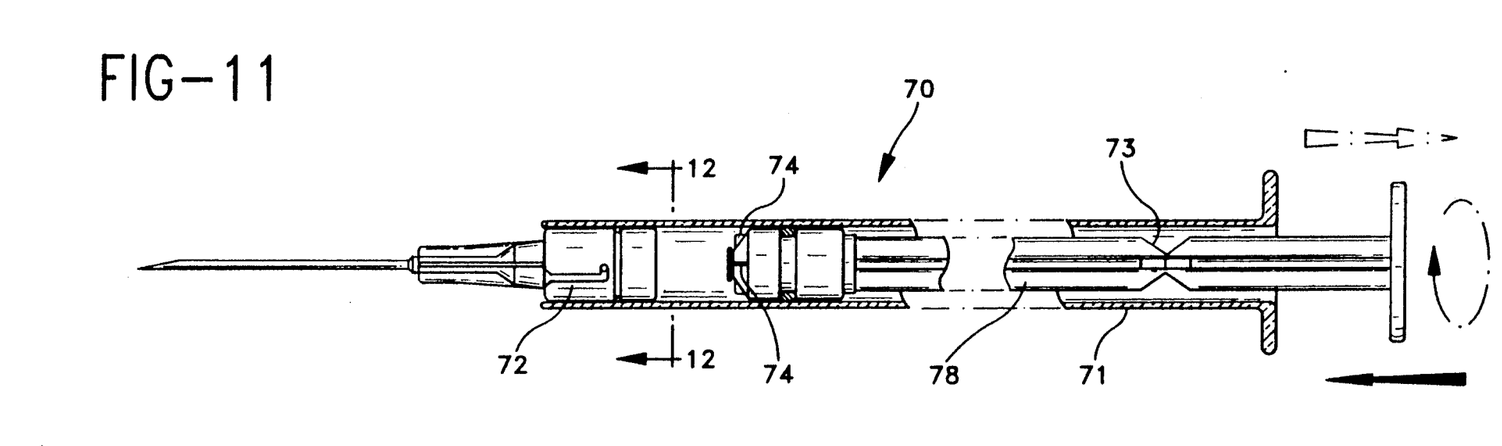
FIG. 11 is a partial cross sectional side elevation view of an alternate embodiment of the safety needle syringe assembly of the present invention.
Figure 12:
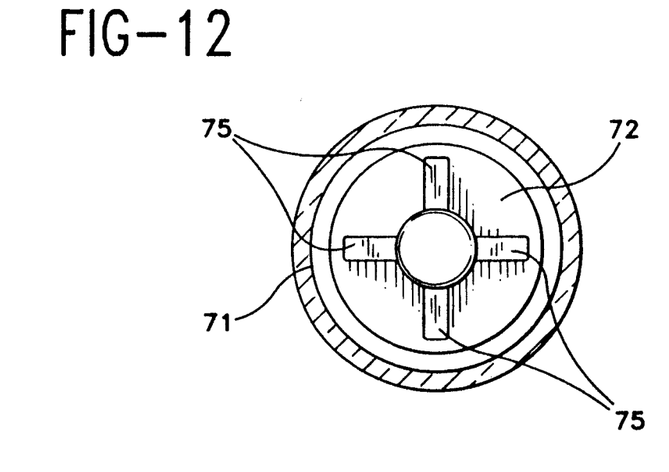
FIG. 12 is a cross-sectional view of the syringe of FIG. 1, taken along line 12—12.

Referring to FIGS. 11 and 12, an alternative embodiment of the safety needle syringe assembly 70 of the present invention is illustrated. This embodiment functions similarly to the embodiment of FIGS. 1-10 except that barrel 71 is substantially cylindrical and has a substantially constant inside diameter at its distal end. Carrier 72 is approximately the diameter of the plunger rod and occludes the distal open end of the barrel. This structure is advantageous for small diameter syringes and for allowing the use of barrels made from constant diameter tubing such as extruded tubing. This structure has the advantage of maintaining a fluid tight seal between the carrier and the barrel as the carrier is withdrawn into the barrel. This embodiment also includes a frangible zone or area of reduced cross section 73 on plunger rod 78 so that the proximal end of the plunger rod can be disconnected from the remainder of the plunger rod after the carrier and needle assembly are safely within barrel 71.

In this embodiment the rotational force to move the carrier from the locked to the unlocked position is transmitted from plunger rod 78 to carrier 72 through the engagement of outwardly extending projections 74 on the plunger which are received by and engage recesses 75 on carrier 72. In this embodiment the combination of four projections and four recesses minimizes the amount of dead space to hold medication which cannot be delivered. The function of this embodiment can be carried out with one or more projections enraging with one or more recesses or protuberances on the carrier in order to transmit rotational force as taught in the embodiments of FIGS. 1-10.

The barrel of the safety needle syringe of the present invention may be constructed of a wide variety of rigid materials with thermoplastic and glass materials being preferred. Inwardly facing projections at the distal end of the barrel may be formed of the barrel material or be formed of additional components made of suitable rigid materials such as thermoplastic and corrosion resistant metal such as stainless steel.

The plunger rod and the carrier of the present invention can be made through a wide variety of rigid materials with thermoplastic materials such as polypropylene, polyethylene and polystyrene being desirable. A wide variety of materials such as natural rubber, synthetic rubber and thermoplastic elastomers are suitable for forming the annular elastomeric ring, the annular sealing ring and the stopper. For embodiments of the present invention which are desirably sterile the materials used for the components should be chosen to withstand the sterilization process utilized.

Thus, it can be seen that the present invention provides a simple, straight forward, reliable, easily fabricated safety needle syringe which allows the user to change needles at the time of use and provide structure to withdraw the needle into the barrel using substantially axial forces such as those used for drawing liquid into the syringe. The present invention also provides locking structure for holding the needle in position with respect to the barrel. This locking structure can be deactivated to lower the force required for withdrawal of the needle into the barrel.

What is claimed is:

1. A safety needle syringe comprising:
   an elongate barrel having an inside surface defining a chamber, an open proximal end and a distal end;
   a movable needle carrier positioned in fluid-tight engagement with said inside surface of said barrel at said distal end of said barrel, said carrier having an outside surface, a distal end, and proximal end, and a passageway therethrough in fluid communication with said chamber;
   a needle cannula projecting outwardly from said distal end of said carrier, said cannula having a distal end and lumen therethrough in fluid communication with said passageway;
   plunger means slidably positioned in fluid-tight engagement with said inside surface of said barrel, said plunger means having a distal end, and a proximal end extending outwardly from said open end of said barrel;
   engagement means for allowing said distal end of said plunger means to engage said carrier for allowing axially directed forces and rotational forces applied to said proximal end of said plunger means to be transmitted to said carrier;
   internal control means within said barrel for helping to prevent movement of said carrier with respect to said barrel during normal use of said syringe while said control means is in a first locked position, and for allowing said carrier to be moved proximally into said chamber through forces applied to said plunger means while said control means is in a second unlocked position, transition between said first locked position and said second unlocked position and withdrawing said cannula into said barrel being accomplished by at least two motions of said plunger means with respect to said barrel while said distal end of said plunger means engages said carrier, said first motion being rotational to rotate said carrier with respect to said barrel through an acute angular rotation followed by a second axial motion proximally directed to move said carrier into said barrel far enough so that said distal end of said cannula does not extend beyond said distal end of said barrel; and
   said control means comprising cooperating structure between said inside surface of said barrel and said outside surface of said carrier including a closed end groove in said outside surface of said carrier or in said inside surface of said barrel.

2. The syringe of claim 1 wherein said distal end of needle cannula includes a sharp edge.

3. The syringe of claim 1 wherein said needle is removably attached to said carrier.

4. The syringe of claim 1 wherein said needle cannula includes a proximal end connected to a hub, said hub being removably connected to said carrier.

5. The syringe of claim 1 wherein said carrier includes an annular elastomeric ring extending around the periphery of said carrier, between said carrier and said barrel for forming a fluid-tight seal between an inside diameter of said barrel and an outside diameter of said carrier.

6. The syringe of claim 1 wherein said engagement means includes a projection on said distal end of said plunger means and a recess in said proximal end of said carrier, said projection being capable of engaging said recess in a snap fit arrangement.

7. The syringe of claim 1 wherein said engagement means includes a distally extending boss having an outwardly extending projection on said plunger means adapted to engage a second inwardly projecting protuberance on a recess in said carrier upon rotation of said plunger means with respect to said carrier.

8. The syringe of claim 1 wherein said plunger means includes an elongate rigid plunger rod having an elastomeric stopper at its distal end, and said engagement means includes a proximally directed projection on said carrier capable of piercing said stopper and engaging said plunger rod.

9. The syringe of claim 1 wherein said control means includes said closed end groove on said carrier, said groove including an open distal end, a projection on said inside surface of said barrel positioned within said groove when said carrier is at said distal end of said barrel, said projection preventing proximal and distal motion of said carrier with respect to said barrel when said projection is in said closed end and allowing proximal motion of said carrier when said projection is in said open end.

10. The syringe of claim 9 wherein said groove in said carrier includes an area of reduced width adjacent to said closed end, said area of reduced width being smaller than the distance across said projection so that additional rotational force is required to move said carrier into and out of a position where said projection is positioned at said closed end of said groove.

11. The syringe of claim 9 wherein said groove in said carrier includes an area of reduced depth adjacent to said closed end, said area of reduced depth being configured so that additional rotational force is required to move said carrier into and out of a position where said projection is positioned at said closed end of said groove.

12. The syringe of claim 9 wherein said projection has a circularly shaped cross section.

13. The syringe of claim 9 further including a second groove in said carrier opposed from said groove and a second projection on said barrel opposed from said projection, said second projection being positioned in said second groove when said carrier is at said distal end of said barrel.

14. The syringe of claim 1 wherein said barrel is made of material selected from the group consisting of thermoplastic and glass.

15. The syringe of claim 1 wherein said plunger means includes a frangible zone between said distal end of said plunger means and said proximal end of said plunger means so that the proximal end of the plunger means can be disconnected from the distal end of the plunger means after said carrier is moved into said barrel far enough so that said distal end of said cannula does not extend beyond said distal end of said barrel.

* * * * *